US009347032B2

(12) United States Patent
Adam

(10) Patent No.: US 9,347,032 B2
(45) Date of Patent: May 24, 2016

(54) COMPOSTER

(71) Applicant: Global Environment Management (FZC), Sharjah Free Zone (AE)

(72) Inventor: Robert James Adam, Sharjah Free Zone (AE)

(73) Assignee: Global Environment Management (FZC), Sharjah Free Zone ( * ) Notice: Subject to any disclaimer, the term of this patent is extended or adjusted under 35 U.S.C. 154(b) by 0 days.

(21) Appl. No.: 14/051,675

(22) Filed: Oct. 11, 2013

(65) Prior Publication Data

US 2014/0106443 A1    Apr. 17, 2014

Related U.S. Application Data

(63) Continuation of application No. PCT/AU2012/000366, filed on Apr. 11, 2012.

(30) Foreign Application Priority Data

Apr. 11, 2011   (AU) ................................ 2011901358

(51) Int. Cl.
*C12M 1/00* (2006.01)
*C12M 1/04* (2006.01)
*C05F 17/02* (2006.01)

(52) U.S. Cl.
CPC ............ *C12M 23/24* (2013.01); *C05F 17/0205* (2013.01); *Y02W 30/43* (2015.05)

(58) Field of Classification Search
CPC ........................... C05F 17/0205; C12M 23/24
USPC ....................................................... 435/290.1
See application file for complete search history.

(56) References Cited

U.S. PATENT DOCUMENTS

| 5,490,604 | A | 2/1996 | Alexander |
| 2002/0081717 | A1 | 6/2002 | Morrison |
| 2003/0024686 | A1* | 2/2003 | Ouellette ........................ 165/47 |
| 2008/0213876 | A1* | 9/2008 | Morrison ................... 435/290.1 |

FOREIGN PATENT DOCUMENTS

| AU | 772528 B2 | | 4/2004 |
| DE | 9114715 U1 | | 4/1992 |
| DE | 4432048 A1 | | 3/1996 |
| WO | WO9725296 | | 7/1997 |
| WO | WO 01/40140 | * | 6/2001 |
| WO | WO2004035508 | | 4/2004 |
| WO | WO2006037152 | | 4/2006 |

OTHER PUBLICATIONS

International Preliminary Report on Patentability for PCT/AU2012/000366, mailed Oct. 24, 2013.
International Search Report for International Application No. PCT/AU2012/000366, mailed Jun. 22, 2012.
Supplementary European Search Report for European Application 12771960, mailed Oct. 17, 2014.

* cited by examiner

*Primary Examiner* — Nathan Bowers
*Assistant Examiner* — Timothy Barlow
(74) *Attorney, Agent, or Firm* — Fish & Richardson P.C.

(57) ABSTRACT

A composter comprising a container for receiving material to be composted, an aerator within the container having at least one opening for allowing air to pass from the aerator into the container, a base structure defining a floor on which the composting material sits above a leachate tank located under the floor, an air flow path through the base structure for providing air from outside the composter to the aerator and to openings located in the floor above the leachate tank to facilitate aerobic decomposition of the composting material.

7 Claims, 6 Drawing Sheets

COMPOSTER

BACKGROUND OF THE INVENTION

Composting is an environmentally friendly way of disposing of waste organic material. Generally in order to provide good compost, it is desirable that the material aerobically decomposes. By providing the right environment for aerobic decomposition, the material can quickly decompose and the quality of the compost is improved.

It is also desirable to collect leachate which drains from the compositing material for separate use or to dispose of rather than to allow the leachate simply to drain to the ground.

Composting containers may come in many shapes and sizes for both domestic and commercial use.

In our earlier patent application WO 2006/037152 we describe a composting apparatus that comprises a plastics container formed of a plurality of segments. The container includes a centrally positioned aerator that allows air from the exterior of the container to distribute into the compositing mass within the container. The container also includes a base which included a leachate chamber for collecting leachate that drains from the composting mass during composting.

This apparatus has proved quite successful but it is considered that there is an opportunity to introduce additional air into the container to improve the aerobic compost decomposition.

It is this issue that has brought about the present invention.

SUMMARY OF THE INVENTION

According to one aspect of the present invention there is provided a composter comprising a container for receiving material to be composted, an aerator within the container and at least one opening for allowing air to pass from the aerator into the container, a base structure defining a floor on which the composting material sits above a leachate tank located under the floor, an air flow path through the base structure for providing air from outside the composter to the aerator and to openings located in the floor above the leachate tank to facilitate aerobic decomposition of the composting material.

Preferably, the base structure includes a plurality of spaced pillars that support the underside of the floor, the pillars facilitating air flow through the floor. Preferably, the pillars extend upwardly from the base of the leachate tank. In a preferred embodiment each pillar has a cut out in its wall facilitating air flow into the leachate tank.

DESCRIPTION OF THE DRAWINGS

An embodiment of the present invention will now be described by way of example only with reference to the accompanying drawings in which.

DESCRIPTION OF THE PREFERRED EMBODIMENT

The composter 10 shown in the accompanying drawings is in many respects very similar to the composter that is the subject of our co-depending patent application WO 2006/037152. More particularly, the composter is similar to the embodiment illustrated in FIGS. 13 and 14 of that application, the disclosure of which is incorporated herein by reference.

Figure 1:
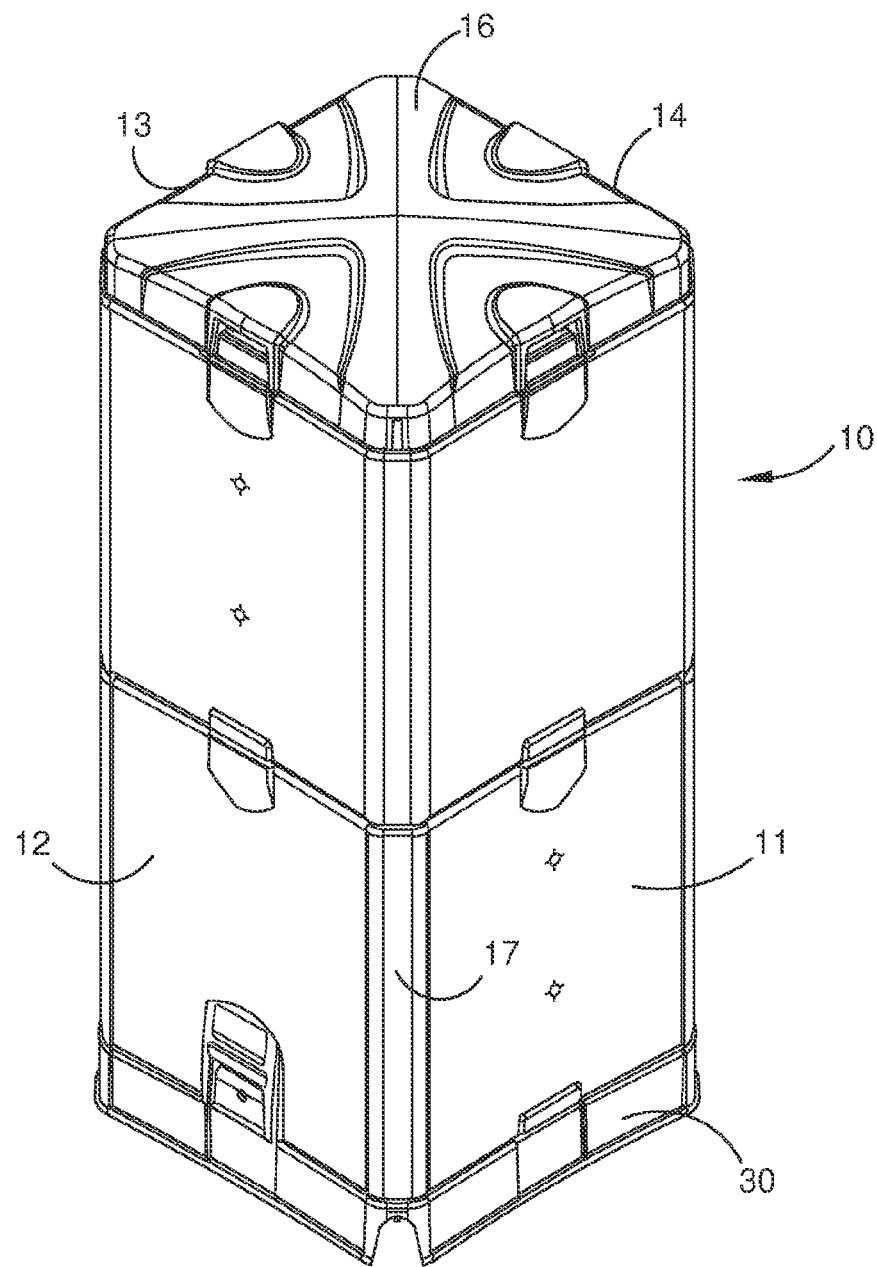
FIG. 1 is a perspective view of a composter.
Figure 2:
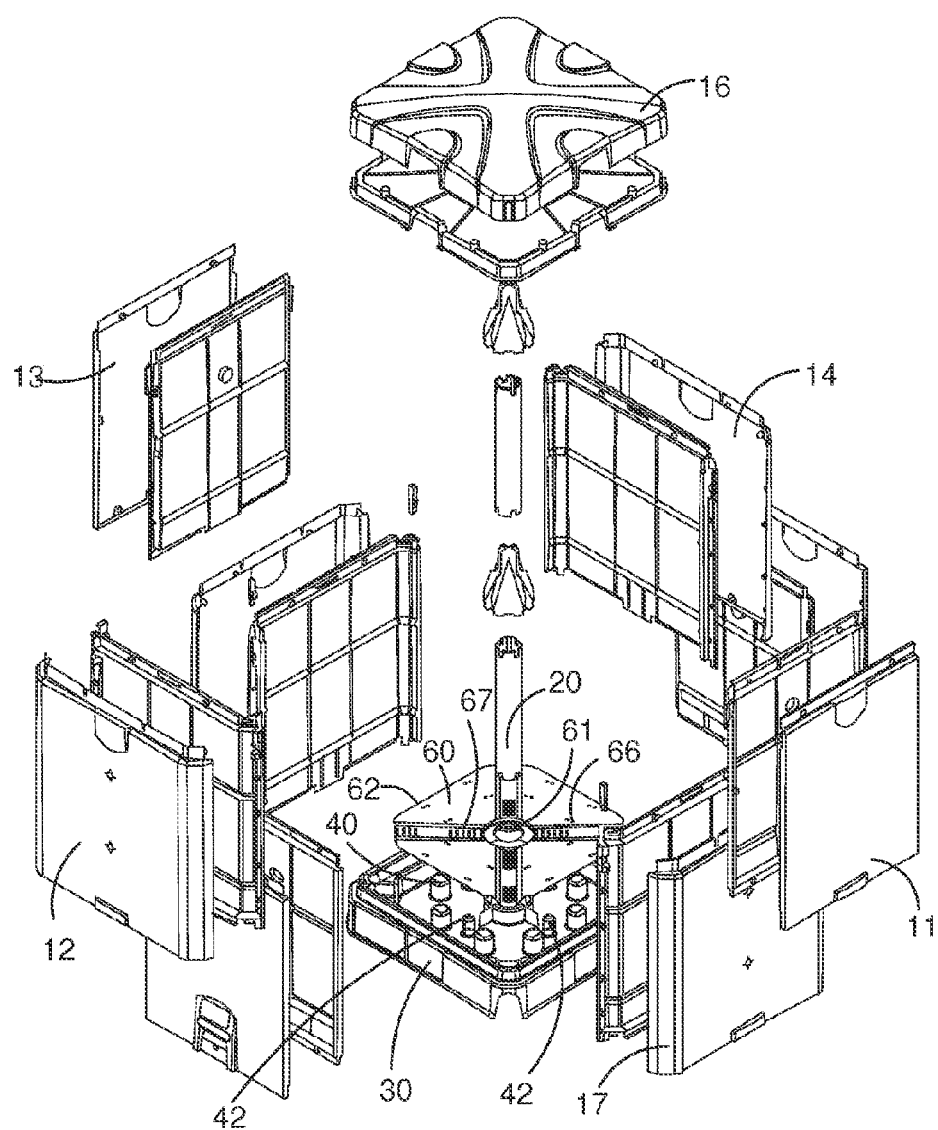
FIG. 2 is an exploded perspective view of the composter.
Figure 3:
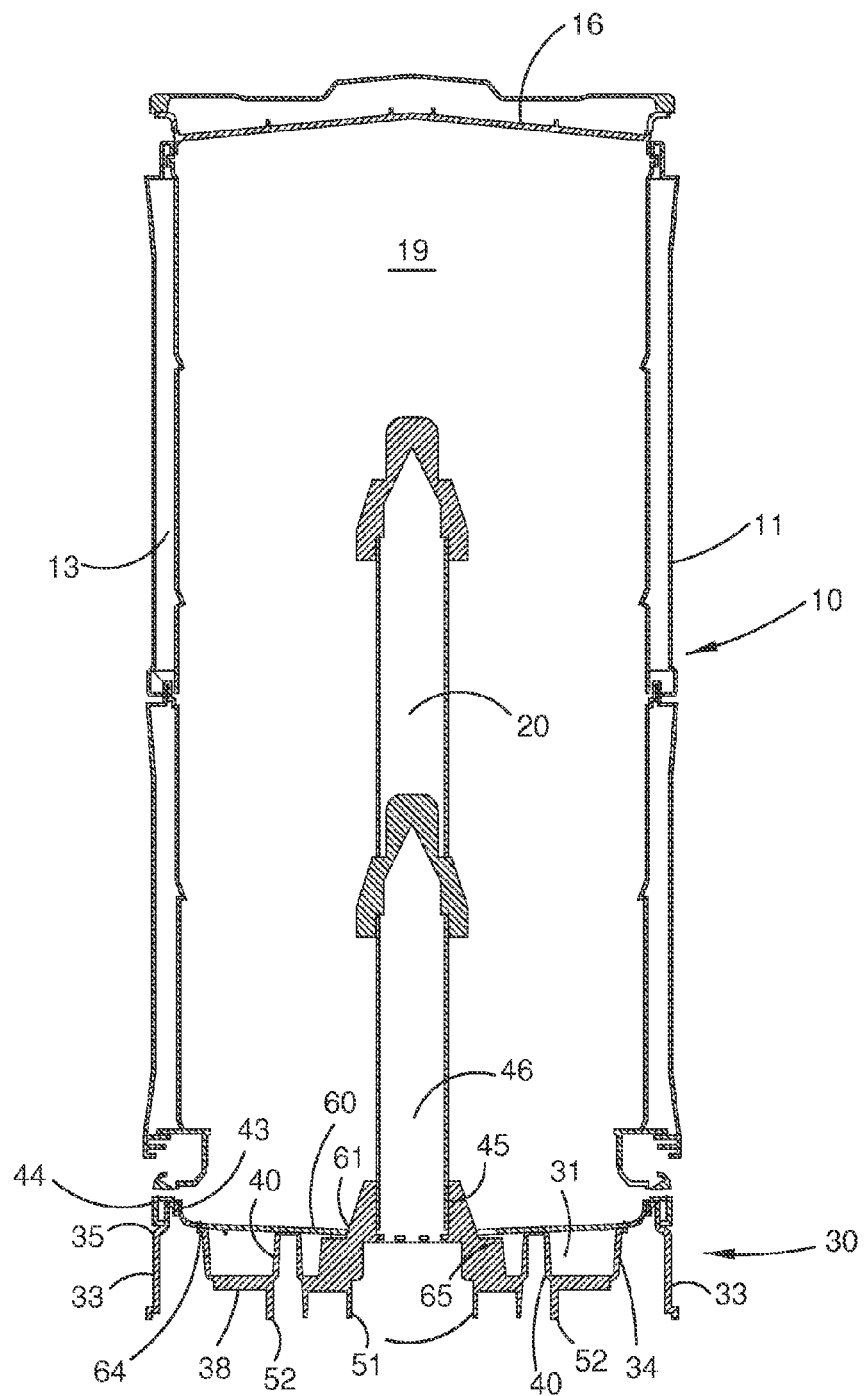
FIG. 3 is a cross sectional view of a composter taken through the base of side walls and the lid showing the components slightly separated.
Figure 4:
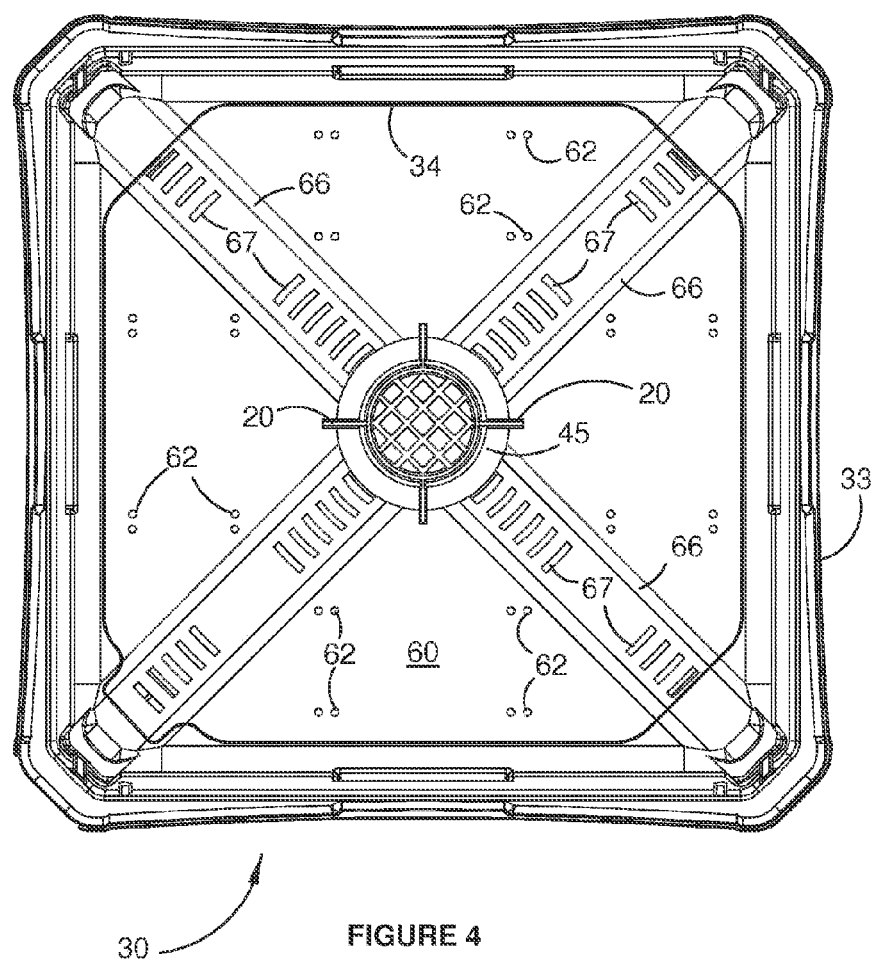
FIG. 4 is a plan view of the base with a base plate fitted.
Figure 5:
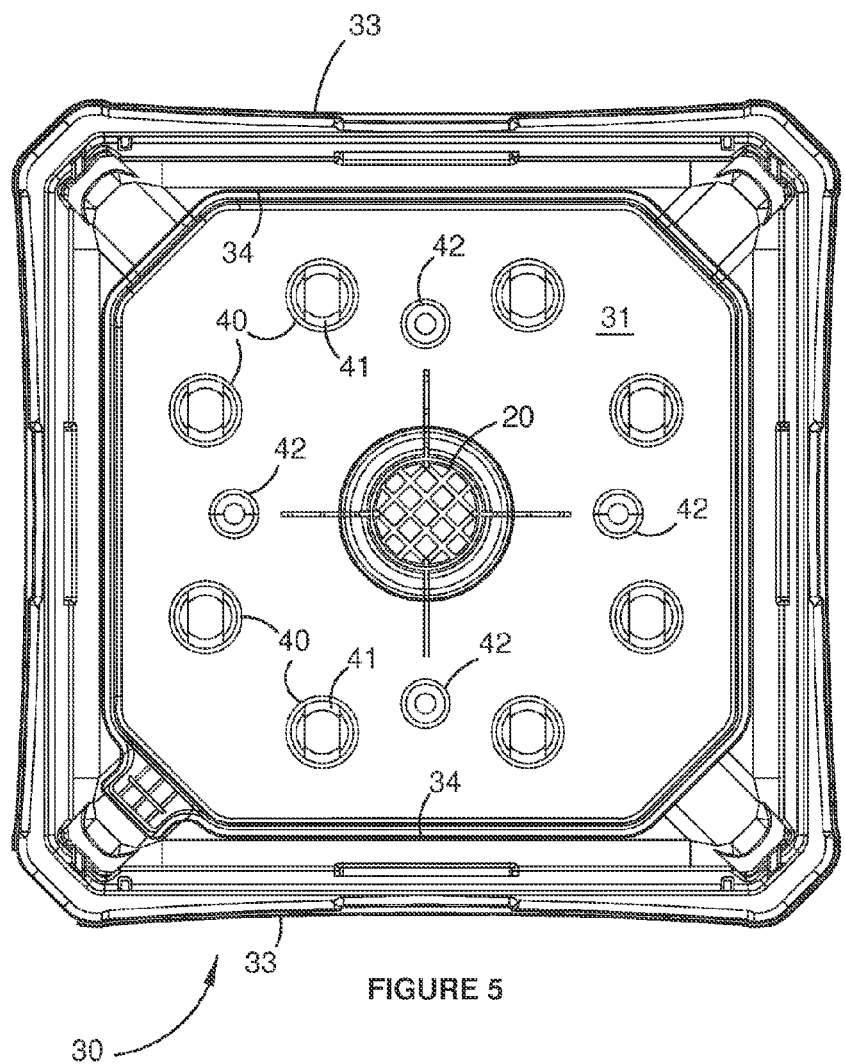
FIG. 5 is a plan view of the base with the base plate removed.
Figure 6:
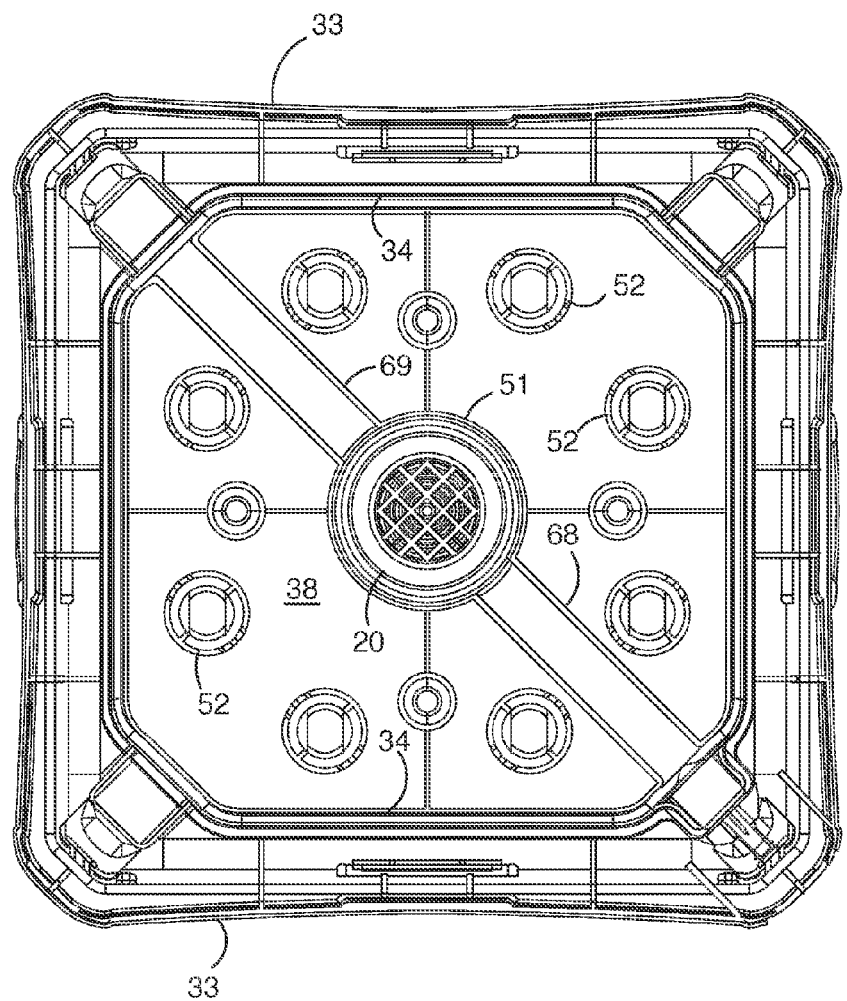
FIG. 6 is an underside view of the base.

The composter 10 shown in FIGS. 1 and 2 essentially comprises a rectangular container 10 having side walls 11, 12, 13 and 14, a base 30 and a lid 16. The join between the side walls includes an inclined joining panel 17 which gives the composter a more rounded configuration. Mounted centrally of the base 30 is an aerator 20 that extends upwardly into the composting enclosure 19 defined by the container. The side walls and lid of the container are moulded in plastics to define a twin walled hollow configuration as shown in FIGS. 2 and 3. The container 10, side walls 11-14, lid 16, and aerator 20 are substantially similar to the components disclosed in WO 2006/037152.

This invention relates to the design of the base 30 which is described in greater detail hereunder.

The base 30 as shown in the cross-sectional view of FIG. 1 comprises a leachate tank 31 and a leachate tank support structure 32 that is moulded in plastics. The moulding defines a peripheral outer wall 33, an inwardly spaced leachate tank 31 having a peripheral wall 34 spaced inwardly from the outer wall 33 of the base structure 30 and terminated on a level slightly below the top 35 of the peripheral wall 33 of the base structure 30. The leachate tank 31 has a substantially horizontal base 38 that includes eight equally spaced upstanding pillars 40 that extend upwardly from the base 38. The centre of the tank includes an upwardly projecting frustoconical spigot 45 that in use supports the stem 46 of the aerator 20. The underside of the leachate tank 31 has downwardly projecting feet in the form of an inner ring 51 underneath the aerator and eight annular feet 52 underneath each pillar 40. The top of the base structure 30 between the outer wall 33 and the wall 34 of the tank 31 includes a raised peripheral rib 43 that, in use, engages an external clamping ring 44 that holds the base structure to the base of the wall structure. The join between the top of the base structure and the external rib in the base of the wall structure is shown exploded in FIG. 3.

The top of the tank 31 is covered by a substantially planar floor 60 that has a central cut out 61 to accommodate the frustoconical spigot 45. The floor 60 has a series of perforations 62 allowing air to escape from the tank 31 into the chamber of the composter. As shown in FIG. 3 the floor locates on a ledge 64 formed at the top of the outer wall 34 of the tank 31 and an annular shoulder 65 formed on the frustoconical spigot 45. The floor 60 is removable, but serves to separate the composting waste from the leachate tank 31. The floor 60 is also supported by the upper ends of the pillars 40 and four supports 42. The pillars 40 include cut outs 41 in the wall structure allowing air to flow out into the leachate tank 31 above the liquid level to then flow through apertures 62 in the floor 60 into the base of the composting chamber 19. The floor 60 has four outwardly extending webs 66 having spaced parallel slots 68 to allow the leachate to drain onto the tank 31.

The underside of the base 38 of the leachate tank 31 includes a pair of diagonal channels 68, 69 that extend from opposite corners across the centre of the composter. These channels 68, 69 allow air to flow from the exterior of the composter 10 along the channels 66, 67 air into the central aerator 20 as shown in FIG. 3. The base of the tank is designed so that there is sufficient ground engaging wall structures to support the structure whilst at the same time facilitate the ready transfer of air for both the aerator and the top of the leachate tank so that it can filter through the base into the bottom of the compositing material.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A composter comprising:
a container for receiving material to be composted;
an aerator within the container having at least one opening for allowing air to pass from the aerator into the container;
a base structure defining a floor on which the composting material sits above a leachate tank located under the floor wherein the aerator is mounted to extend upwardly of the base structure;
a plurality of upstanding pillars that extend upwardly from a base of the leachate tank and into the leachate tank, the pillars facilitating air flow through the floor; and
an air flow path through the base structure, for providing air from outside the composter into the pillars and through cut outs in the pillars through which air flows into the leachate tank above a leachate liquid level and to openings located in the floor above the leachate tank to facilitate aerobic decomposition of the composting material.

2. The composter according to claim 1 wherein the pillars are spaced to support the underside of the floor.

3. The composter according to claim 1 wherein the base structure includes a perforated floor panel which in use supports the composting material.

4. The composter according to claim 1 wherein an air inlet allows air to enter the composter and flow through one or more air channels beneath the floor and enter the container through one or more holes in the floor.

5. The composter according to claim 4 wherein conduits direct air from beneath the floor to the holes in the floor.

6. The composter according to claim 1 wherein air flows from the outside of the composter through channels in the base structure and into the aerator.

7. The composter according to claim 4 wherein the holes in the floor are provided across a substantial portion of the floor to facilitate aerobic decomposition of the composting material across the floor.

* * * * *